United States Patent
Que et al.

(10) Patent No.: US 8,940,929 B2
(45) Date of Patent: Jan. 27, 2015

(54) PREPARATION METHOD OF HIGH-OPTICAL PURITY N2-[1-(S)-ETHOXYCARBONYL-3-PHENYLPROPYL]-N6-TRIFLUOROACETYL-L-LYSINE

(75) Inventors: Limin Que, Jiangsu (CN); Yueheng Jiang, Jiangsu (CN); Zhigang Lin, Jiangsu (CN); Tong Cai, Jiangsu (CN)

(73) Assignee: ABA Chemicals Corporation, Taicang, Jiangsu (CN)

( * ) Notice: Subject to any disclaimer, the term of this patent is extended or adjusted under 35 U.S.C. 154(b) by 51 days.

(21) Appl. No.: 13/822,690

(22) PCT Filed: Sep. 29, 2010

(86) PCT No.: PCT/CN2010/077478
§ 371 (c)(1),
(2), (4) Date: Mar. 13, 2013

(87) PCT Pub. No.: WO2012/040922
PCT Pub. Date: Apr. 5, 2012

(65) Prior Publication Data
US 2013/0178651 A1 Jul. 11, 2013

(30) Foreign Application Priority Data
Sep. 28, 2010 (CN) .......................... 2010 1 0294700

(51) Int. Cl.
C07C 229/00 (2006.01)
C07C 51/42 (2006.01)
C07C 231/20 (2006.01)

(52) U.S. Cl.
CPC ............... *C07C 51/42* (2013.01); *C07C 231/20* (2013.01); *C07B 2200/07* (2013.01)
USPC ........................................................ 562/450

(58) Field of Classification Search
CPC .... C07C 233/47; C07C 229/08; C07C 229/34
See application file for complete search history.

(56) References Cited

U.S. PATENT DOCUMENTS

| 5,136,044 A | 8/1992 | Inoue et al. | |
|---|---|---|---|
| 6,118,010 A * | 9/2000 | Ueda et al. | 548/532 |
| 2004/0147773 A1* | 7/2004 | Iida et al. | 560/38 |
| 2005/0075508 A1* | 4/2005 | Fukae et al. | 549/292 |

FOREIGN PATENT DOCUMENTS

| CN | 101239923 | 8/2008 |
|---|---|---|
| JP | 6336495 | 12/1994 |
| JP | 200326644 | 1/2003 |
| WO | 9743246 | 11/1997 |
| WO | 03006421 | 1/2003 |

OTHER PUBLICATIONS

Ueda et al. (Chemical Engineering Research and Design, 2007, 85(A3), 406).*
Partial English Translation of Su et al. (CN 101239923) 2008.*
STN abstract of Su et al. (CN 101239923) 2008.*
International Search Report of PCT/CN2010/077478 dated Jun. 23, 2011.

* cited by examiner

*Primary Examiner* — Rosalynd Keys
*Assistant Examiner* — Jennifer C Sawyer
(74) *Attorney, Agent, or Firm* — Rankin, Hill & Clark LLP

(57) ABSTRACT

Disclosed is a preparation method of high-optical purity N2-[1-(S)-ethoxycarbonyl-3-phenylpropyl]-N6-trifluoroacetyl-L-lysine. The method includes: adding crude N2-[1-(S)-ethoxycarbonyl-3-phenylpropyl]-N6-trifluoroacetyl-L-lysine to one or more organic solvents, and then reacting with an organic acid to form a salt, which is precipitated, thereby achieving the purpose of separation and purification; next, adding the obtained solid or mother concentrate into deionized water, and then adding an inorganic base or an organic base for basification, so as to adjust the pH value, removing the organic acid, filtering, washing and drying, to obtain the high-optical purity N2-[1-(S)-ethoxycarbonyl-3-phenylpropyl]-N6-trifluoroacetyl-L-lysine, where the molar ratio of 1S-isomer to 1R-isomer is equal to or greater than 99:1.

10 Claims, 2 Drawing Sheets

PREPARATION METHOD OF HIGH-OPTICAL PURITY N2-[1-(S)-ETHOXYCARBONYL-3-PHENYLPROPYL]-N6-TRIFLUOROACETYL-L-LYSINE

TECHNICAL FIELD

The present invention relates to the field of chiral drug preparation technologies, and in particular to a preparation method of a chiral drug Lisinopril intermediate N2-[1-(S)-ethoxycarbonyl-3-phenylpropyl]-N6-trifluoroacetyl-L-lysine, and more particularly, to a purification method of high-optical purity N2-[1-(S)-ethoxycarbonyl-3-phenylpropyl]-N6-trifluoroacetyl-L-lysine.

BACKGROUND OF THE INVENTION

Lisinopril, as shown in FIG. 1, is a lysine derivate of Enalapril, and belongs to the third-generation long-acting angiotensin-converting enzyme inhibitor (ACEI). Lisinopril inhibits the renin-angiotensin-aldosterone system to reduce the blood pressure, and at the same time, it also has an antihypertension effect on low-rennin hypertension. Lisinopril has the advantages that the acting duration is long, the trough-to-peak ratio of reduced systolic pressure and diastolic pressure is high, the antihypertension effect is stable, and no liver lesion is caused because Lisinopril is not converted by liver after oral administration and absorption, so Lisinopril is superior to other drugs for patients with liver diseases and hepatic dysfunction. Presently, Lisinopril has become one of drugs of choice for treatment of hypertension.

N2-[1-(S)-ethoxycarbonyl-3-phenylpropyl]-N6-trifluoroacetyl-L-lysine is a key intermediate for synthesis of Lisinopril, and has a structural formula shown in FIG. 2. Michael addition of N6-trifluoroacetyl-L-lysine to β-ethyl benzoylacrylate followed by catalytic hydrogenation, provides a crude mixture of N2-[1-ethoxycarbonyl-3-phenylpropyl]-N6-trifluoroacetyl-L-lysine with a diastereomeric ratio of 80:20 SS/RS, respectively. Patents of JP1986/68970, JP1991/22867, JP1992/4308, JP1994/336495 and WO1997/043246 disclose processes for preparations of similar compounds. The 1R-isomer is the main impurity, and has a structural formula shown in FIG. 3. WO1997/043246 does not disclose any method for purifying and isolating the 1S-isomer, and does not disclose a method for removing the undesired 1R-isomer. The crude products are directly applied to the subsequent reaction, and the yield of the final product is lower, and at the same time, the cost of the raw material and the production cost are increased. JP1986/68970 and JP1992/4308 disclose a recrystallization method using water and ethanol, but the yield is low. JP2003/026644 discloses a purification method of re crystallization using water with a water-soluble solvent such as acetonitrile or tetrahydrofuran by gradient cooling where 1R-isomer is removed. However, good solubility of N2-[1-ethoxycarbonyl-3-phenylpropyl]-N6-trifluoroacetyl-L-lysine in acetonitrile or tetrahydrofuran results in lower yield of recrystallization, and it becomes more obvious on large quantity production. Additionally, it is difficult to control gradient cooling on manufacturing scale, and acetonitrile and tetrahydrofuran are relatively expensive solvents.

SUMMARY OF THE INVENTION

It is an object of the present invention to provide a simple, efficient and economic process for preparing optically pure N2-[1-(S)-ethoxycarbonyl-3-phenylpropyl]-N6-trifluoroacetyl-L-lysine.

Technical solution: in order to achieve the objective, the present invention adopts the following technical solution.

A method for preparing high-optical purity N2-[1-(S)-ethoxycarbonyl-3-phenylpropyl]-N6-trifluoroacetyl-L-lysine, which includes the following steps:

(1) Crude N2-[1-(S)-ethoxycarbonyl-3-phenylpropyl]-N6-trifluoroacetyl-L-lysine is added to an organic solvent at a mass-to-volume ratio of 1:1~50, with the temperature being controlled at −20~50° C., an organic acid is added to the reaction solution and the reaction mixture is stirred for 5 to 24 hrs. A salt is formed and precipitates. Filtration and concentration to dryness under a reduced pressure at a temperature lower than 40° C. provides a concentrate mother liquor; For the crude N2-[1-(S)-ethoxycarbonyl-3-phenylpropyl]-N6-trifluoroacetyl-L-lysine, the molar ratio of the 1S-isomer to the 1R-isomer is 80:20; the molar ratio of the organic acid to the crude N2-[1-(S)-ethoxycarbonyl-3-phenylpropyl]-N6-trifluoroacetyl-L-lysine is 0.5~1.5:1.

(2) The solid or concentrated mother liquor obtained in Step (1) is added to deionized water at a weight-to-volume ratio of 1:1~25, and the temperature is controlled at −20~50° C. An inorganic or organic base is added to adjust the pH to 4.0~6.0. The resulting mixture is cooled to 0 to 5° C., and stirred for 3 hrs. After filtering, washing, and drying, optically pure N2-[1-(S)-ethoxycarbonyl-3-phenylpropyl]-N6-trifluoroacetyl-L-lysine is obtained with 1S-isomer/1R-isomer≥99/1.

For further understanding of the content of the present invention, the present invention is specifically described as follows:

Crude N2-[1-(S)-ethoxycarbonyl-3-phenylpropyl]-N6-trifluoroacetyl-L-lysine rich in 1S isomer may be prepared by ethyl β-benzoylacrylate and N6-trifluoroacetyl-L-lysine through Michael addition, and then subjected to catalytic hydrogenation. In the product obtained through the method, the molar ratio of the 1S-isomer to the 1R-isomer is 80:20.

The organic solvents employed in the invention are selected from fatty acid esters, ketones, ethers and hydrocarbons such as ethyl formate, propyl formate, butyl formate, methyl acetate, ethyl acetate, propyl acetate, butyl acetate, isopropyl acetate, isobutyl acetate, pentyl acetate, isopentyl acetate, methyl propanoate, ethyl propanoate, propyl propanoate, butyl propanoate, pentyl propanoate, acetone, 2-butanone, cyclopentanone, cyclohexanone, ethyl ether, propyl ether, isopropyl ether, methyl tert-butyl ether, tetrahydrofuran, 1,4-dioxane, n-hexane, cyclohexane, methylcyclohexane and n-heptane or a mixture thereof at any ratio, and preferably a mixed solvent of fatty acid esters and hydrocarbons.

The volumes of the organic solvents employed in the invention are 1 to 50 folders and preferably 5 to 10 folders of the mass of the crude N2-[1-(S)-ethoxycarbonyl-3-phenylpropyl]-N6-trifluoroacetyl-L-lysine rich in 1S-isomer.

The organic acids employed in the invention have a structure represented by general formula (I):

$$Ar'SO_3H \quad (I)$$

wherein Ar represents aryl. Aryl is phenyl or alkyl substituted phenyl. When aryl is phenyl, the organic acid is benzenesulfonic acid, and when aryl is alkyl substituted phenyl, the organic acid may be o-methyl benzenesulfonic acid, m-methyl benzenesulfonic acid, p-methyl benzenesulfonic acid, o-ethyl benzenesulfonic acid, m-ethyl benzenesulfonic acid, p-ethyl benzenesulfonic acid or benzenesulfonic acid substituted by other alkyls.

The aryl-sulfonic acid may react with the crude N2-[1-ethoxycarbonyl-3-phenylpropyl]-N6-trifluoroacetyl-L-lysine mixture rich in 1S-isomer to form sulfonate salts. The N2-[1-(S)-ethoxycarbonyl-3-phenylpropyl]-N6-trifluoroacetyl-L-lysinearyl sulfonate is precipitated where 1R-sulfonate is soluble in the organic solvent and remains in the solution. By separating the solid from the mixture, purification and isolation of the desired 1S-isomer is achieved, thereby achieving the purpose of separation and purification.

The molar ratio of the organic acid, namely, aryl-sulfonic acid, to the crude N2-[1-(S)-ethoxycarbonyl-3-phenylpropyl]-N6-trifluoroacetyl-L-lysine rich in 1S-isomer is 0.2~1.5:1, and preferably 0.8~1.2:1.

The organic acids of the present invention further have a structures represented by general formula (II)

$$HOOC(CH_2)_nCOOH \quad (II)$$

wherein n=0, 1 or 2. When n=0, the organic acid is oxalic acid, when n=1, the organic acid is malonic acid, and when n=2, the organic acid is succinic acid.

A di-acid having a structure represented by general formula (II) may react with the crude N2-[1-ethoxycarbonyl-3-phenylpropyl]-N6-trifluoroacetyl-L-lysine rich in 1S-isomer to form a salt. The N2-[1-(R)-ethoxycarbonyl-3-phenylpropyl]-N6-trifluoroacetyl-L-lysine carboxylic salt is precipitated where the 1S-isomer salt is soluble in the organic solvent and remains in the solution. By separating the 1R-isomersalt from the mixture, purification of 1S-isomer is achieved.

The molar ratio of the organic acid, namely, the binary acid, to the crude N2-[1-(S)-ethoxycarbonyl-3-phenylpropyl]-N6-trifluoroacetyl-L-lysine rich in 1S-isomer is 0.2~1.5:1, and preferably 0.25~0.75:1.

The organic acid of general formula (I) selectively reacts with the 1S-isomer in the crude N2-[1-ethoxycarbonyl-3-phenylpropyl]-N6-trifluoroacetyl-L-lysine rich in 1S-isomer to form a salt, which is precipitated and separated to give a mother liquid rich in 1R isomer. Subsequently, the binary acid having a structure represented by general formula (II) may selectively react with the 1R-isomer of the mother liquor to form a salt, which is precipitated and separated to give a mother liquid rich in 1S-isomer. For the N2-[1-ethoxycarbonyl-3-phenylpropyl]-N6-trifluoroacetyl-L-lysine mixture rich in 1S-isomer, the method of the present invention may be continuously adopted to give pure N2-[1-(S)-ethoxycarbonyl-3-phenylpropyl]-N6-trifluoroacetyl-L-lysine as shown in FIG. 4.

Beneficial effects: By applying the organic acid salt-forming method of the present invention, N2-[1-(S)-ethoxycarbonyl-3-phenylpropyl]-N6-trifluoroacetyl-L-lysine is obtained with 1S-isomer/1R-isomer≥99:1. Inexpensive and readily available raw materials, simple operations, and no special requirement on equipments make the present invention suitable for large-scale industrial production.

DETAILED DESCRIPTION

Figure 1:
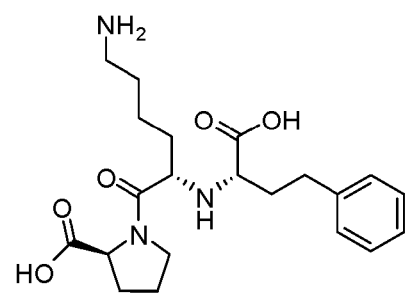
FIG. 1 shows a structural formula of Lisinopril.
Figure 2:
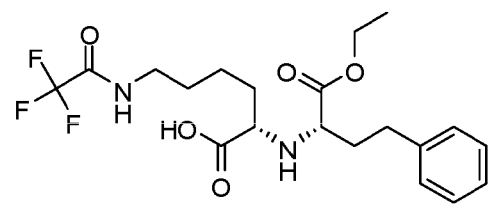
FIG. 2 shows a structural formula of the 1S-isomer of N2-[1-(S)-ethoxycarbonyl-3-phenylpropyl]-N6-trifluoroacetyl-L-lysine.
Figure 3:
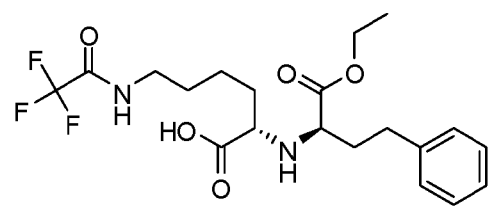
FIG. 3 shows a structural formula of the 1R-isomer of N2-[1-(S)-ethoxycarbonyl-3-phenylpropyl]-N6-trifluoroacetyl-L-lysine.
Figure 4:
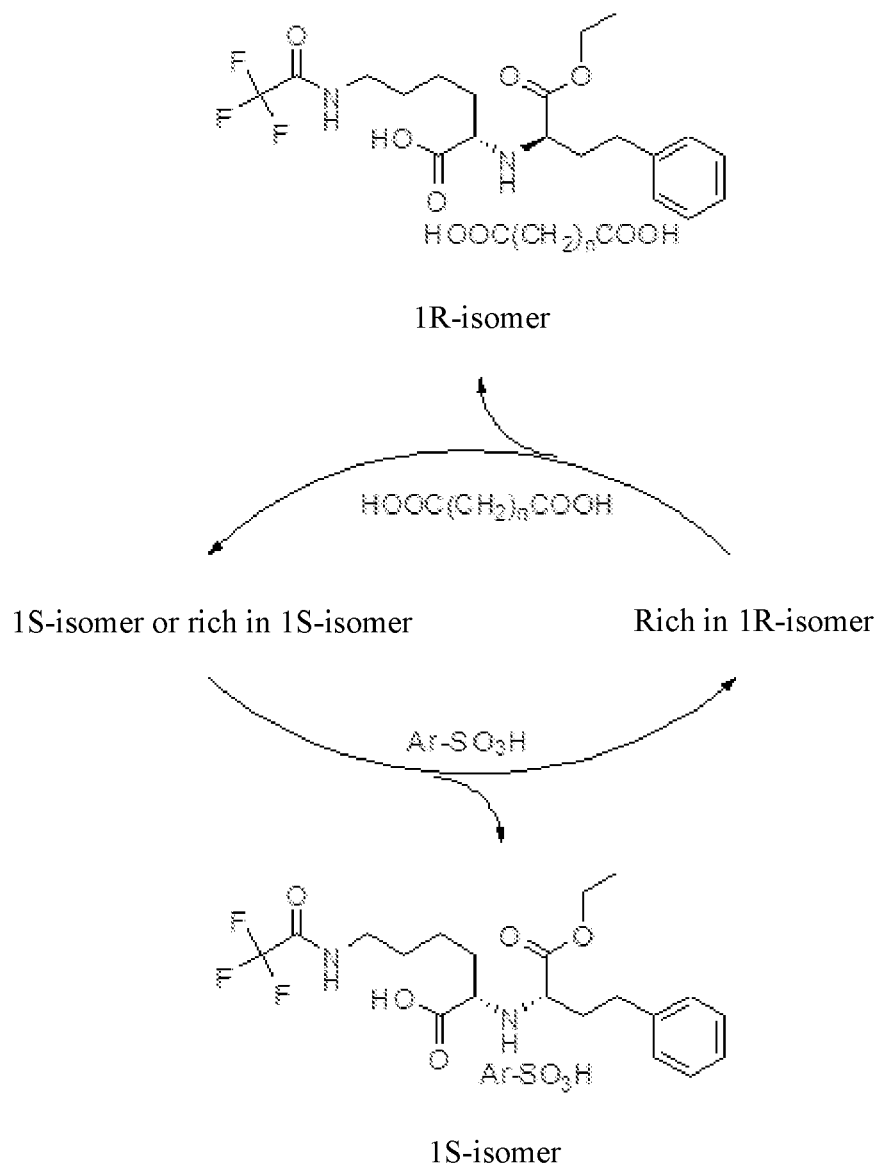
FIG. 4 is a schematic view of cyclic salt forming by adopting a mother liquid of an aryl-sulfonic acid having a structure represented by General Formula (I) and a binary acid having a structure of General Formula (II).

The present invention is further described below with reference to specific embodiments.

Embodiment 1

10 g of crude N2-[1-(S)-ethoxycarbonyl-3-phenylpropyl]-N6-trifluoroacetyl-L-lysine rich in 1S-isomer (the molar ratio of the 1S- to the 1R-isomer was 80:20) was suspended in 10-fold volume mixed solvents of 80 ml of ethyl acetate and 20 ml of n-hexane. 4.4 g (1.0 eq.) of p-methylbenzenesulfonic acid monohydrate was added, and the reaction mixture was stirred at room temperature for 10 hrs. The mixture was filtered, and the solid was dried under a vacuum at a temperature lower than 40° C. The solid was dissolved in 80 ml of water, and 1N sodium hydroxide solution was added to adjust the pH value to 4.0 to 6.0. The reaction system was cooled to 0 to 5° C., and then stirred for 3 hrs and filtered, and the resulting solid was dried under a vacuum at a temperature lower than 40° C. to give 7.6 g of pure N2-[1-(S)-ethoxycarbonyl-3-phenylpropyl]-N6-trifluoroacetyl-L-lysine. The yield is 76%, and the molar ratio of the 1S- to the 1R-isomer is 99.2:0.8.

Embodiments 2 to 20

The operations were the same as those in Embodiment 1, except that different types and ratios of organic solvents were adopted. The detailed results are shown in Table 1

TABLE 1

Results of Embodiments 2 to 20

| | Type and Ratio of Organic Solvent | Yield | Molar Ratio of the 1S-isomer to the 1R-isomer |
|---|---|---|---|
| Embodiment 2 | Ethyl acetate 100 ml | 46.5% | 99.7:0.3 |
| Embodiment 3 | Ethyl acetate 80 ml + cyclohexane 20 ml | 74.5% | 99.6:0.4 |
| Embodiment 4 | Ethyl acetate 80 ml + methylcyclohexane 20 ml | 76.3% | 99.1:0.9 |
| Embodiment 5 | Ethyl acetate 80 ml + n-heptane 20 ml | 77.0% | 99.0:1.0 |
| Embodiment 6 | Isopropyl acetate 100 ml | 41.5% | 99.6:0.4 |
| Embodiment 7 | Isopropyl acetate 80 ml + n-hexane 20 ml | 75.1% | 99.1:0.9 |
| Embodiment 8 | Isopropyl acetate 80 ml + cyclohexane 20 ml | 75.2% | 99.2:0.8 |
| Embodiment 9 | Isopropyl acetate 80 ml + methylcyclohexane 20 ml | 76.2% | 99.5:0.5 |
| Embodiment 10 | Isopropyl acetate 80 ml + n-heptane 20 ml | 75.8% | 99.4:0.6 |
| Embodiment 11 | Butyl acetate 100 ml | 39.5% | 99.7:0.3 |
| Embodiment 12 | Butyl acetate 80 ml + n-hexane 20 ml | 72.2% | 99.2:0.8 |
| Embodiment 13 | Butyl acetate 80 ml + cyclohexane 20 ml | 71.2% | 99.2:0.8 |
| Embodiment 14 | Butyl acetate 80 ml + methylcyclohexane 20 ml | 71.9% | 99.0:1.0 |
| Embodiment 15 | Butyl acetate 80 ml + n-heptane 20 ml | 72.2% | 99.3:0.7 |

TABLE 1-continued

Results of Embodiments 2 to 20

|  | Type and Ratio of Organic Solvent | Yield | Molar Ratio of the 1S-isomer to the 1R-isomer |
|---|---|---|---|
| Embodiment 16 | Acetone 80 ml + n-heptane 20 ml | 64.6% | 99.6:0.4 |
| Embodiment 17 | Tetrahydrofuran 80 ml + n-heptane 20 ml | 53.2% | 99.8:0.2 |
| Embodiment 18 | Ethyl acetate 70 ml + n-hexane 30 ml | 82.6% | 97.2:2.8 |
| Embodiment 19 | Ethyl acetate 60 ml + n-hexane 40 ml | 86.5% | 94.6:5.4 |
| Embodiment 20 | Ethyl acetate 40 ml + n-hexane 60 ml | 89.6% | 88:12 |

Embodiments 21 to 24 the operations were the same as those in Embodiment 1, except that different solvents volumes were adopted. The detailed results are shown in Table 2.

TABLE 2

Detailed results of Embodiments 21 to 24

|  | Ratio of Organic Solvent | Yield | Molar Ratio of the 1S-isomer to the 1R-isomer |
|---|---|---|---|
| Embodiment 21 | 1-fold volume | 86.6% | 89.7:10.3 |
| Embodiment 22 | 5-fold volume | 77.5% | 98.9:1.1 |
| Embodiment 23 | 20-fold volume | 66.7% | 99.4:0.6 |
| Embodiment 24 | 50-fold volume | 55.4% | 99.3:0.7 |

Embodiments 25 to 28 the operations were the same as those in Embodiment 1, except that different equivalents of p-methylbenzenesulfonic acid was adopted. The detailed results are shown in Table 3.

TABLE 3

Detailed results of Embodiments 25 to 28

|  | Ratio of p-Methyl-benzenesulfonic Acid | Yield | Molar Ratio of the 1S-isomer to the 1R-isomer |
|---|---|---|---|
| Embodiment 25 | 0.50 equivalent weight | 36.5% | 99.7:0.3 |
| Embodiment 26 | 0.75 equivalent weight | 47.5% | 99.6:0.4 |
| Embodiment 27 | 1.20 equivalent weight | 76.3% | 99.0:1.0 |
| Embodiment 28 | 1.50 equivalent weight | 85.0% | 90:10 |

Embodiment 29

10 g of crude N2-[1-ethoxycarbonyl-3-phenylpropyl]-N6-trifluoroacetyl-L-lysine rich in 1S-isomer (the molar ratio of the 1S- to the 1R-isomer was 80:20) was suspended in 10-fold volume mixed solutions of 80 ml of ethyl acetate and 20 ml of n-hexane. 1.46 g (0.5 eq.) of oxalic acid monohydrate was added, and the reaction mixture was stirred at room temperature for 24 hrs. The reaction mixture was filtered, and the filtrate was concentrated to dryness under reduced pressure at a temperature lower than 40° C. The filtered cake was dissolved in 80 ml water, and 1N sodium hydroxide solution was added to adjust the pH value to 4.0 to 6.0. The solution was cooled to 0 to 5° C., and stirred for 3 hrs. After filtration, and the solid was dried in vacuum at a temperature lower than 40° C. to give 5.8 g of pure N2-[1-(S)-ethoxycarbonyl-3-phenyl-propyl]-N6-trifluoroacetyl-L-lysine. The yield is 58%, and the molar ratio of the 1S- to the 1R-isomer is 99.0:1.0.

Embodiments 30 to 45 the operations were the same as those in Embodiment 29, except that different types and ratios of organic solvents were adopted. The detailed results are shown in Table 4.

TABLE 4

Detailed results of Embodiments 30 to 45

|  | Type and Ratio of Organic Solvent | Yield | Molar Ratio of the 1S-isomer to the 1R-isomer |
|---|---|---|---|
| Embodiment 30 | Ethyl acetate 80 ml + cyclohexane 20 ml | 54.5% | 99.2:0.8 |
| Embodiment 31 | Ethyl acetate 80 ml + methylcyclohexane 20 ml | 53.5% | 99.4:0.6 |
| Embodiment 32 | Ethyl acetate 80 ml + n-heptane 20 ml | 56.4% | 99.1:0.9 |
| Embodiment 33 | Isopropyl acetate 80 ml + n-hexane 20 ml | 55.5% | 99.2:0.8 |
| Embodiment 34 | Isopropyl acetate 80 ml + cyclohexane 20 ml | 54.4% | 99.0:1.0 |
| Embodiment 35 | Isopropyl acetate 80 ml + methylcyclohexane 20 ml | 56.8% | 99.2:0.8 |
| Embodiment 36 | Isopropyl acetate 80 ml + n-heptane 20 ml | 54.9% | 99.3:0.7 |
| Embodiment 37 | Butyl acetate 80 ml + n-hexane 20 ml | 53.2% | 99.1:0.9 |
| Embodiment 38 | Butyl acetate 80 ml + cyclohexane 20 ml | 52.1% | 99.1:0.9 |
| Embodiment 39 | Butyl acetate 80 ml + methylcyclohexane 20 ml | 52.0% | 99.2:0.8 |
| Embodiment 40 | Butyl acetate 80 ml + n-heptane 20 ml | 51.2% | 99.1:0.9 |
| Embodiment 41 | Acetone 100 ml | 69.7% | 89:11 |
| Embodiment 42 | Tetrahydrofuran 100 ml | 89.0% | 86:14 |
| Embodiment 43 | Ethyl acetate 70 ml + n-hexane 30 ml | 41.8% | 99.5:0.5 |
| Embodiment 44 | Ethyl acetate 60 ml + n-hexane 40 ml | 45.5% | 99.2:0.8 |
| Embodiment 45 | Ethyl acetate 40 ml + n-hexane 60 ml | 39.9% | 99.6:0.4 |

Embodiments 46 to 49 the operations were the same as those in Embodiment 29, except different organic solvents were adopted. The detailed results are shown in Table 5.

TABLE 5

Detailed results of Embodiments 46 to 49

|  | Ratio of Organic Solvent | Yield | Molar Ratio of the 1S-isomer to the 1R-isomer |
|---|---|---|---|
| Embodiment 46 | 1-fold volume | 36.2% | 99.8:0.5 |
| Embodiment 47 | 5-fold volume | 48.2% | 99.1:0.9 |
| Embodiment 48 | 20-fold volume | 68.5% | 99.0:1.0 |
| Embodiment 49 | 50-fold volume | 85.3% | 89.5:10.5 |

Embodiments 50 to 52 the operations were the same as those in Embodiment 29, except that different equivalents of oxalic acid was adopted. The detailed results are shown in Table 6.

TABLE 6

Detailed results of Embodiments 50 to 52

|  | Ratio of Oxalic Acid Hydrate | Yield | Molar Ratio of the 1S-isomer to the 1R-isomer |
|---|---|---|---|
| Embodiment 50 | 0.25 equivalent weight | 86.5% | 95:5 |
| Embodiment 51 | 0.75 equivalent weight | 47.2% | 99.1:0.9 |
| Embodiment 52 | 1.00 equivalent weight | 35.3% | 99.4:0.6 |

Embodiment 53

10 g of crude N2-[1-ethoxycarbonyl-3-phenylpropyl]-N6-trifluoroacetyl-L-lysine rich in 1S-isomer (the molar ratio of the 1S- to the 1R-isomer was 80:20) was suspended in 10-fold volume mixed solutions of 80 ml of ethyl acetate and 20 of ml n-hexane. 1.2 g (0.5 eq.) of malonic acid was added, the reaction mixture was stirred at −10 to 0° C. for 16 hrs. The reaction mixture was filtered, and the filtrate was concentrated to dryness under reduced pressure at a temperature lower than 40° C. The residual solid was dissolved in 100 ml of water, and 1N sodium hydroxide solution was added to adjust the pH value to 4.5. The reaction mixture was cooled to 0 to 5° C., and stirred for 3 hrs. After filtration, the solid was dried in vacuum at a temperature lower than 40° C. to give 6.8 g of pure N2-[1-(5)-ethoxycarbonyl-3-phenylpropyl]-N6-trifluoroacetyl-L-lysine. The yield is 68%, and the molar ratio of the 1S- to the 1R-isomer is 99.0:1.0.

Embodiment 54

The mother liquid obtained in Embodiment 16 was concentrated to dryness, and 50 ml of water was added. 1N sodium hydroxide solution was added to adjust the pH value to 4.5. The reaction mixture was cooled to 0 to 5° C., and stirred for 3 hrs. After filtration, and the resulting solid was dried in vacuum at a temperature lower than 40° C. to give 3.35 g of solid with a molar ratio of the 1S- to the 1R-isomer of 41:59. The solid was suspended in 27 ml of ethyl acetate and 6 ml of n-hexane, and 0.4 g (0.5 eq.) of malonic acid was added. The reaction mixture was stirred at room temperature for overnight. After filtration, the filtrate was concentrated to dryness under reduced pressure at a temperature lower than 40° C. The filter cake was dissolved in 80 ml of water, and 1N sodium hydroxide solution was added to adjust the pH value to 4.5. The resulting solution was cooled to 0 to 5° C., and stirred for 3 hrs and filtered. The resulting solid was dried in vacuum at a temperature lower than 40° C. to give 1.6 g of solid with a molar ratio of the 1S- to the 1R-isomer of 84:16. The solid was then suspended in 12 ml of ethyl acetate and 3 ml of n-hexane, and 0.7 g (1.0 eq.) p-methylbenzenesulfonic acid monohydrate was added. The reaction mixture was stirred at room temperature till the solid was dissolved and a clear solution was obtained. The reaction mixture was stirred for additional 5 hrs at −10 to 0° C. After filtration, the filter cake was dried under a vacuum at a temperature lower than 40° C. The solid was dissolved in 20 ml of water, and 1N sodium hydroxide solution was added to adjust the pH value to 4.5. The reaction system was cooled to 0 to 5° C., and stirred for 3 hrs. After filtration, and the filter cake was dried under a vacuum at a temperature lower than 40° C. to give 1.3 g of pure N2-[1-(S)-ethoxycarbonyl-3-phenylpropyl]-N6-trifluoroacetyl-L-lysine with a molar ratio of the 1S- to the 1R-isomer of 99.4:0.6.

Combined with the product of Embodiment 16, the total yield is 78.0%.

Embodiment 55

The operations were the same as those in Embodiment 1, except that the whole reaction was performed at a different temperature, such as −20° C., −10° C., 0° C., 10° C., 30° C. and 50° C., and the solid or mother liquid was added to deionized water at a mass-to-volume ratio of 1:1, 1:10, 1:15, and 1:25. Under those conditions, the reaction proceeded, and pure N2-[1-(S)-ethoxycarbonyl-3-phenylpropyl]-N6-trifluoroacetyl-L-lysine was obtained.

What is claimed is:

1. A method for preparation high-optical purity N2-[1-(S)-ethoxycarbonyl-3-phenylpropyl]-N6-trifluoroacetyl-L-lysine, comprising:

(1) adding crude N2-[1-(S)-ethoxycarbonyl-3-phenylpropyl]-N6-trifluoroacetyl-L-lysine to an organic solvent at a mass-to-volume ratio of 1:1~50, at the temperature of −20 to 50° C., adding an organic acid to the reaction system, and then carrying out a reaction for 5 to 24 hours with stirring, so that a salt is formed and precipitated as a solid; filtering the reaction mixture, and concentrating the filtrate to dryness under a reduced pressure at a temperature lower than 40° C., to obtain a mother concentrate, wherein the molar ratio of the 1S-isomer to the 1R-isomer of the crude N2-[1-(S)-ethoxycarbonyl-3-phenylpropyl]-N6-trifluoroacetyl-L-lysine is 80:20; and the molar ratio of the organic acid to the crude N2-[1-(S)-ethoxycarbonyl-3-phenylpropyl]-N6-trifluoroacetyl-L-lysine is 0.5 to 1.5:1;

(2) adding the solid or the mother concentrate obtained in Step (1) to deionized water at a weight-to-volume ratio of 1:1~25, at a temperature of −20~50° C., adding an inorganic or an organic base for basification, and adjusting the pH value to 4.0~6.0, cooling the reaction mixture to 0~5° C., and stirring the reaction solution for 3 hours, then after filtering, washing, and drying, the high-optical purity N2-[1-(S)-ethoxycarbonyl-3-phenylpropyl]-N6-trifluoroacetyl-L-lysine is obtained with a molar ratio of the 1S-isomer to the 1R-isomer to be equal to or greater than 99:1.

2. The method for preparing high-optical purity N2-[1-(S)-ethoxycarbonyl-3-phenylpropyl]-N6-trifluoroacetyl-L-lysine according to claim 1, wherein the organic solvent is one of fatty acid esters, ketones, ethers and hydrocarbons or a mixture thereof at any ratio, and comprises ethyl formate, propyl formate, butyl formate, methyl acetate, ethyl acetate, propyl acetate, butyl acetate, isopropyl acetate, isobutyl acetate, pentyl acetate, isopentyl acetate, methyl propanoate, ethyl propanoate, propyl propanoate, butyl propanoate, pentyl propanoate, acetone, 2-butanone, cyclopentanone, cyclohexanone, ethyl ether, propyl ether, isopropyl ether, methyl tert-butyl ether, tetrahydrofuran, 1,4-dioxane, n-hexane, cyclohexane, methylcyclohexane and n-heptane or a mixture thereof at any ratio.

3. The method for preparing high-optical purity N2-[1-(S)-ethoxycarbonyl-3-phenylpropyl]-N6-trifluoroacetyl-L-lysine according to claim 1, wherein the organic acid has a structure represented by General Formula (I): Ar—SO$_3$H, and Ar is aryl, comprising phenyl or alkyl substituted phenyl.

4. The method for preparing high-optical purity N2-[1-(S)-ethoxycarbonyl-3-phenylpropyl]-N6-trifluoroacetyl-L-lysine according to claim 1, wherein the molar ratio of the organic acid to the crude N2-[1-(S)-ethoxycarbonyl-3-phenylpropyl]-N6-trifluoroacetyl-L-lysine is 0.8~1.2:1.

5. The method for preparing high-optical purity N2-[1-(S)-ethoxycarbonyl-3-phenylpropyl]-N6-trifluoroacetyl-L-lysine according to claim 1, wherein the organic acid has a structure represented by General Formula (II): HOOC(CH$_2$)nCOOH, wherein n=0, 1 or 2.

6. The method for preparing high-optical purity N2-[1-(S)-ethoxycarbonyl-3-phenylpropyl]-N6-trifluoroacetyl-L-lysine according to claim 1, wherein the molar ratio of the organic acid to the crude N2-[1-(S)-ethoxycarbonyl-3-phenylpropyl]-N6-trifluoroacetyl-L-lysine is 0.25~0.75:1.

7. The method for preparing high-optical purity N2-[1-(S)-ethoxycarbonyl-3-phenylpropyl]-N6-trifluoroacetyl-L-lysine according to claim 1, wherein the inorganic base is sodium hydroxide, potassium hydroxide, barium hydroxide or lithium hydroxide.

8. The method for preparing high-optical purity N2-[1-(S)-ethoxycarbonyl-3-phenylpropyl]-N6-trifluoroacetyl-L-lysine according to claim 1, wherein the organic base is a water soluble amine, comprising diethylamine, triethylamine, triethylene diamine, diisopropylene amine, pyridine, 4-metylpyridine and 4-dimethylaminopyridine.

9. The method for preparing high-optical purity N2-[1-(S)-ethoxycarbonyl-3-phenylpropyl]-N6-trifluoroacetyl-L-lysine according to claim 1, wherein the pH value of the system after basification is 4.5~5.5.

10. The method for preparing high-optical purity N2-[1-(S)-ethoxycarbonyl-3-phenylpropyl]-N6-trifluoroacetyl-L-lysine according to claim 1, wherein in Step (1), the organic acid is of general formula (I): Ar—SO$_3$H wherein Ar is aryl, comprising phenyl or alkyl substituted phenyl, such that the organic acid of general formula (I) selectively reacts with the crude N2-[1-ethoxycarbonyl-3-phenylpropyl]-N6-trifluoroacetyl-L-lysine rich in 1S-isomer to form a salt, which is precipitated as a solid, the method further comprising:

filtering the solid to give a mother liquid which is rich in 1R isomer, selectively reacting the 1R-isomer in the mother liquid with a dicarboxylic acid of general formula (II): HOOC(CH$_2$)nCOOH, wherein n=0, 1 or 2, to form a second salt which is precipitated as a second solid, filtering the second solid to give a second mother liquid which is 1S-isomer N2-[1-(S)-ethoxycarbonyl-3-phenylpropyl]-N6-trifluoroacetyl-L-lysine or N2-[1-ethoxycarbonyl-3-phenylpropyl]-N6-trifluoroacetyl-L-lysine rich in 1S-isomer.

\* \* \* \* \*